United States Patent [19]

Suzuki et al.

[11] Patent Number: 4,568,344
[45] Date of Patent: Feb. 4, 1986

[54] WAIST BAND FOR DISPOSABLE DIAPER

[75] Inventors: Migaku Suzuki, Kawanoe; Mitsuzo Ochi, Ehime; Takeshi Kudo, Kawanoe, all of Japan

[73] Assignee: Uni-Charm Corporation, Ehime, Japan

[21] Appl. No.: 561,478

[22] Filed: Dec. 14, 1983

[30] Foreign Application Priority Data

Dec. 15, 1982 [JP] Japan ................... 57-219828

[51] Int. Cl.⁴ ............................................. A41B 13/02
[52] U.S. Cl. ................................. 604/389; 604/390
[58] Field of Search .................... 604/389, 390

[56] References Cited

U.S. PATENT DOCUMENTS

| | | | |
|---|---|---|---|
| 3,800,796 | 4/1974 | Jacob | 604/390 |
| 3,937,221 | 2/1976 | Tritsch | 604/390 |
| 3,985,136 | 10/1976 | Cepuritis | 604/390 |
| 4,036,233 | 7/1977 | Kozak | 604/389 |
| 4,063,559 | 12/1977 | Tritsch | 604/390 |
| 4,237,889 | 12/1980 | Gobran | 604/389 |

Primary Examiner—John D. Yasko
Assistant Examiner—Sherri E. Vinyard
Attorney, Agent, or Firm—Fred Philpitt

[57] ABSTRACT

Here is disclosed a waist band for diaper to connect the front and rear waists at each side. In contrast with the pressure-sensitive adhesive tape of prior art which necessarily forms an overlapping portion of said front and rear waists at each side of the diaper when the latter is put on the user, this waist band has not only a function to adjust a circumferential dimension of the waist but also the fastening function of the conventional adhesive tape. The waist band disclosed herein has a relatively large length including an area of low rigidity (or high flexibility) serving for said adjusting function and another area of high rigidity serving for said fastening function. Furthermore, this waist band is made of basic material consisting of nonwoven fabric having high flexibility and plastic film which is at least partially melted into said nonwoven fabric integrally therewith so that said area serving for fastening function may have a desired high rigidity.

6 Claims, 13 Drawing Figures

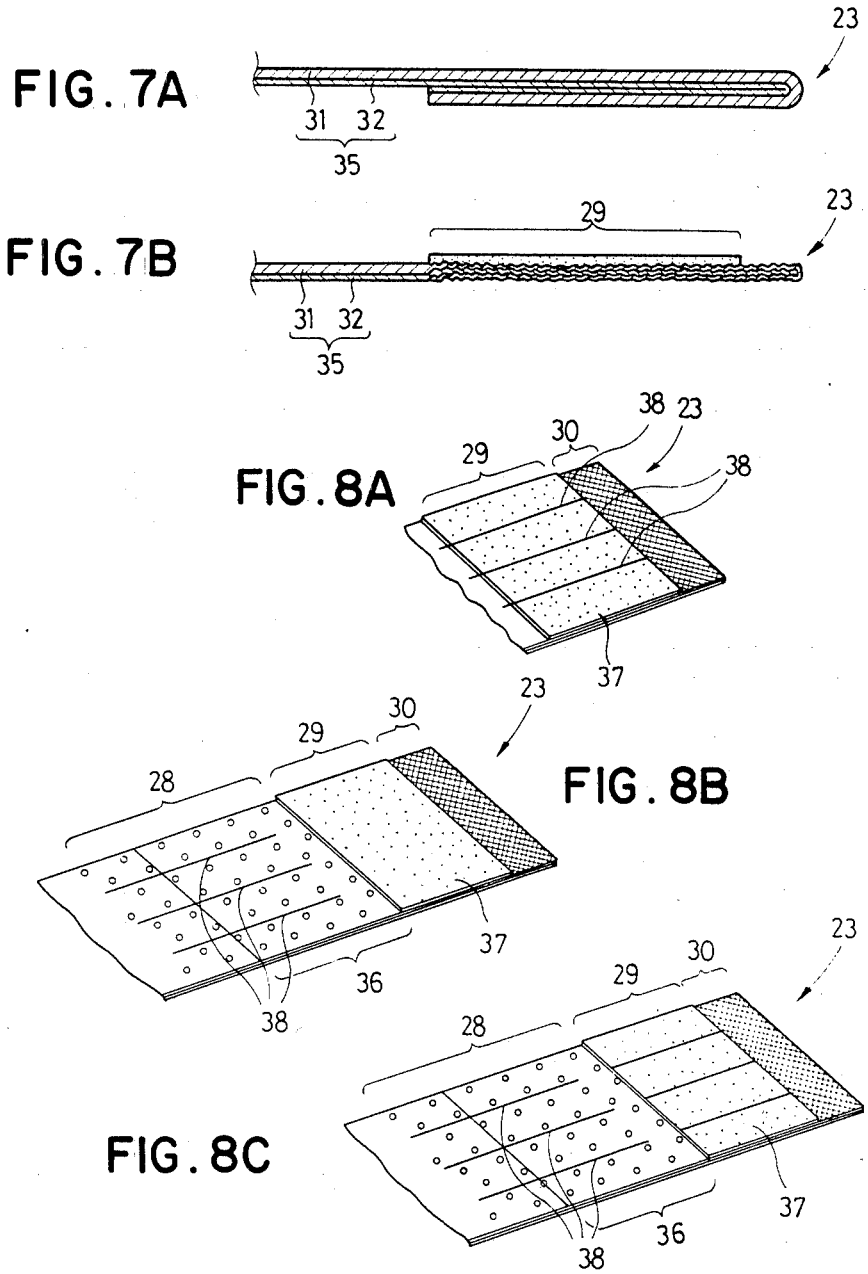

WAIST BAND FOR DISPOSABLE DIAPER

BACKGROUND OF THE INVENTION

It is known to provide the disposable diaper with pressure-sensitive adhesive tape servieng to connect, at the waist level, front and rear areas of the diaper at laterally opposite side ends. In fact, there have already been available from many manufacturers the diapers utilizing such adhesive tape as so easily found in Patent Gazettes or the like that it appears unnecessary to quote these prior arts.

However, such adhesive tape of well known art functions merely to connect said front and rear areas of the diaper at the waist level and at laterally opposite side ends. More specifically, such well known adhesive tape is used for fastening the respective side ends of said rear area in overlapping state with respect to the corresponding side ends of said front area of the diaper when put on the user. Accordingly, this adhesive tape is made of well known material having a relatively high rigidity such as paper-based material and formed in a relative small length sufficient for said fastening function.

With the diaper provided with such adhesive tape, the front and rear areas must be overlapped to each other at opposite side margins in said front and rear areas at the waist level when put on the user. However, these mutually overlapping side margins are considered to have no direct contribution to the diaper's primary function of holding excrements and absorbing liquid ingredients thereof, so that the diaper should be oversized by a dimension corresponding to said overlapping side margins. This should lead to a correspondingly increased material to be used for each diaper and, therefore, to an increased cost. Said overlapping side margins further may cause a bulkiness at opposite sides of the user's waist and may obstruct a free movement of the user.

In the diaper equipped with adhesive tape of well known art as mentioned above, there is separately provided release tape serving to protect the effective surface of said adhesive tape and adapted to be fixed to a surface of the diaper or to be provisionarily attached to said effective surface of said adhesive tape, when said adhesive tape is not used. However, provision of such release tape, in addition to said adhesive tape, correspondingly increases as well the diaper's cost.

Nevertheless, the prior art concerning the disposable diaper teaches or suggests no measure to eliminate the inconveniences as has been described above.

OBJECTS OF THE INVENTION

An object of the present invention is to provide a waist band for a disposable diaper which permits adjustment of the length of said waist without the formation of overlapping side margins at opposite sides of said waist (as has been the case in the diaper of prior art) but maintaining the fastening function of the conventional adhesive tape wherein an area contributing to the former function has a high flexibility (or a low rigidity) and an area contributing to the latter function has a high rigidity, namely, a waist band having quite different functions and comprising areas of quite different rigidities.

Another object of the present invention is to provide a waist band for a disposable diaper which eliminates the demand for separately providing a release tape serving to protect an adhesive surface of the waist band.

A further object of the present invention is to provide a waist band for a disposable diaper having a reliable fastening function which is not deteriorated even by movement of the user.

Still another object of the present invention is to provide a waist band for a disposable diaper causing substantially no damage to the backsheet of the diaper.

Other objects of the present invention will be apparent from the following detailed description of the invention more in detail.

SUMMARY OF THE INVENTION

According to the present invention, the above mentioned objects are achieved by a waist band for a disposable diaper including a topsheet, a backsheet, an absorbent core interposed between said both sheets and a waist band connected to a rear waist at each side and extending outwardly beyond the associated side, said waist band comprising: said waist band including, as basic material, nonwoven fabric and plastic film superposed on one another with said nonwoven fabric being on a side confronting the user's body; said basic material having a first area corresponding to a predetermined length extending from a side end of said rear waist towards a free end of said basic material and constructed to have a low rigidity and a second area extending from the outer end of said first area to the outer end of said basic material and constructed to have a high rigidity; said high rigidity of said second area being achieved by at least melting said plastic film into said nonwoven fabric so as to be integrated therewith; and said first area having said low rigidity being a bridge-like area while said second area having said high rigidity supporting on said nonwoven fabric thereof an adhesive sub-area and a nonadhesive handling sub-area extending outside said adhesive sub-area, wherein said bridge-like area is provided on said nonwoven fabric thereof with a release sub-area having an extent at least equal to that of said adhesive sub-area so that said adhesive sub-area may be provisionarily attached to said nonwoven fabric surface of said bridge-like area. In a preferred embodiment, said waist band is 20 to 80 mm wide, extending outwardly from the side end of said rear waist over a length of 70 to 130 mm, and said bridge-like area, said adhesive sub-area and said handling sub-area have length of 40 to 80 mm, 20 to 40 mm and 5 to 15 mm, respectively; said low rigidity is 0.27 to 33.8 at the value according to the provisions of JIS (Japanese Industrial Standard) - p.8143–1967 while said high rigidity is 2.16 to 15.6 at said value.

BRIEF DESCRIPTION OF THE DRAWINGS

FIG. 7A is a fragmentary section in an enlarged scale illustrating another embodiment of the waist band constructed according to the present invention as before the component materials are laminated to form the area of high rigidity;

FIG. 7B is a view similar to FIG. 7A but as after said component materials have been laminated and thereby said area of high rigidity has been formed;

FIG. 8A is a fragmentary perspective view illustrating a manner in which the waist band of the invention is provided in the adhesive sub-area with slits;

FIG. 8B is a view similar to FIG. 8A but illustrating a manner in which the waist band of the invention is provided in the nonadhesive area with slits;

FIG. 8C is a view similar to FIG. 8A but illustrating a manner in which the waist band of the invention is provided both in the bridge-like area and in the adhesive sub-area with these slits;

DETAILED DESCRIPTION OF THE INVENTION

Figure 1:
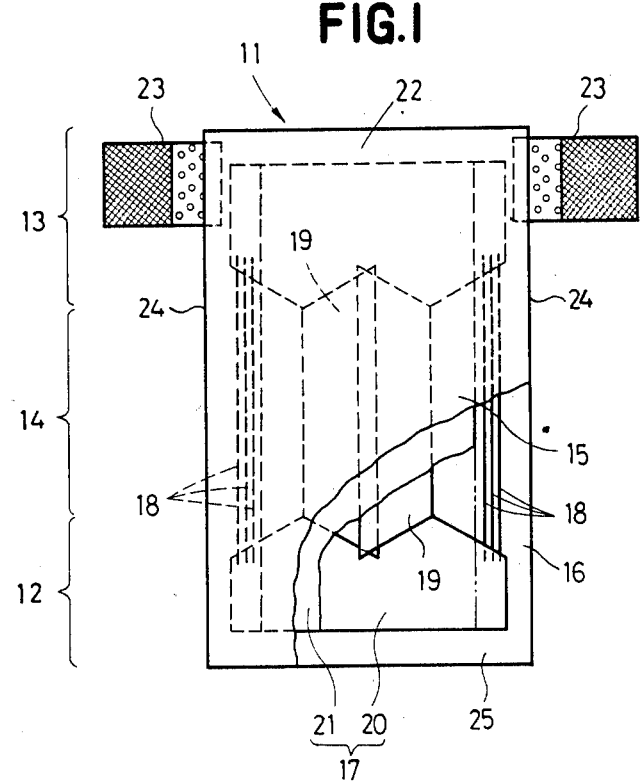
FIG. 1 is a developed plan view, partially broken away, illustrating by way of example a disposable diaper provided with the waist band according to the present invention.
Figure 2:
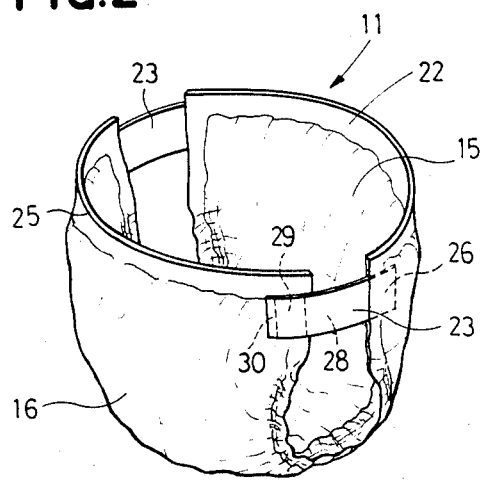
FIG. 2 is a perspective view illustrating the diaper of FIG. 1 as put together.
Figure 3:
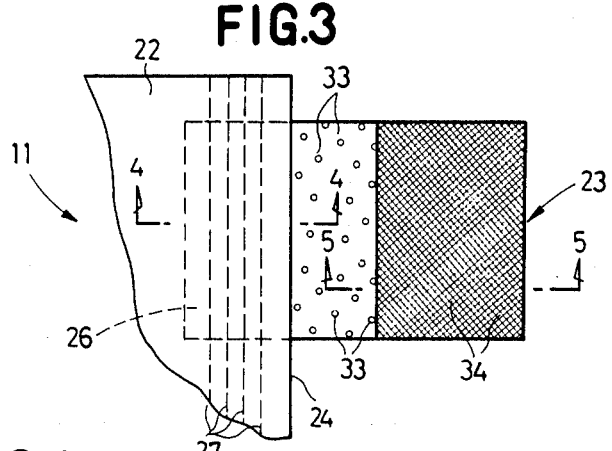
FIG. 3 is a fragmentary plan view illustrating, in an enlarged scale, a portion at which the waist band according to the present invention is attached to the diaper.

FIGS. 1 and 2 illustrate by way of example a disposable diaper provided with a waist band constructed according to the present invention. A diaper 11 basically comprises a front area 12, a rear area 13 and a crotch area 14, and includes a water-pervious topsheet 15 of nonwoven fabric or like as its basic material, a water-impervious backsheet 16 of plastic film or like as its basic material, an absorbent core 17 of fluffy pulp or like as its basic material and interposed between said both sheets 15, 16, and elastic members 18 extending longitudinally of the diaper 11 along opposite sides of said absorbent core 17 between said both sheets 15, 16. The absorbent core 17 consists of a first absorbent member 20 having side flaps 19 inwardly folded in the crotch area 14 and a second absorbent member 21 wider than the crotch area 14 in which said first absorbent member 20 is inwardly folded but narrower than portions of said member 20 in the front and rear areas 12, 13. The elastic members 18 each comprises a plurality of rubber strands being attached to the diaper 11 by elastic hot-melt adhesive of well known type at intervals transversely of the diaper 11. These rubber strands may be 2 to 45 strands and used at elongation percentage of 100 to 400% when these rubber strands have a unit cross-section of 0.03 to 0.45 mm$^2$ and a total cross-section of 0.06 to 1.35 mm$^2$. Although such elastic member 18 is one of the most preferables, a relatively narrow single rubber tape or a relatively wider strip of polyurethane foam both commonly employed in the diaper of this type may be also effectively used.

A waist 22 defined in the rear area 13 of the diaper 11 is provided at each lateral side with a waist band 23 of the invention. The waist band 23 extends outwards beyond the associated lateral end 24 of the diaper 11 by 70 to 130 mm. Those skilled in the art will notice that the waist band 23 is considerably longer than the pressure-sensitive adhesive tape conventionally attached to the diaper of such type. Formation of the waist band 23 in such a manner enables the diaper 11 to have a width narrower than that of the conventional diaper so that, when the diaper 11 is set up so as to be put on the user, gaps formed between the rear waist 22 and the front waist 25 at opposite lateral sides thereof may be bridged by the respective waist bands 23 and thereby the overlap portions occurring in the conventional diaper may be replaced by said bridged portions.

FIGS. 3 through 6 illustrates the waist band 23 more in detail. The waist band 23 is attached to the diaper 11 by interposing an attachment area 26 between the topsheet 15 and the backsheet 16 and integrally welding said area 26 to said two components. Such attachment obviously may be achieved by adhesive and in the event said welding is employed it is preferred to employ a supersonic welding along lines as indicated by broken lines 27. The adhesive tape for the diaper well known and practically utilized is always attached to the diaper on the outer surface of the backsheet 16 and, in consequence, a portion of the backsheet adjacent said attachment area 26 including this area is forcibly stretched under a tension of the adhesive tape during its use, resulting in that said backsheet has its initial strength reduced or is sometimes even damaged. To reinforce said portion adjacent the attachment area, there have already been provided and realized several measures. For example, U.S. Pat. No. 3,867,940 discloses a measure in which the portion of the backsheet to which the adhesive tape is attached is provided on the inner surface with a piece of scrim attached thereto; U.S. Pat. No. 4,055,182 discloses a measure in which the attachment area of the adhesive tape itself is coated on the inner surface with a hot-melt layer; and U.S. Pat. No. 3,848,594 discloses a measure in which the adhesive tape and the mold release tape are attached together to the diaper so that both tapes form a Y-shape at the outer end of the diaper. Attachment means of the waist band 23 according to the present invention, on the contrary, permits the attachment area 26 to be satisfactorily fixed to the diaper without employing any of those measures as disclosed in said prior art and permits said portion adjacent the attachment area inclusive of this attachment area itself to maintain an adequate tensile strength.

The waist band 23 includes, in order from one end to the other end, the attachment area 26, a bridge-like area 28, an adhesive sub-area 29 and a handling sub-area 30. Preferably, the attachment area may have a length $L_1$ at least of 15 mm, the bridge-like area 28 may have a length $L_2$ of 40 to 80 mm, the adhesive sub-area 29 may have a length $L_3$ of 20 to 40 mm, the handling sub-area 30 may have a length $L_4$ of 5 to 15 mm and the waist band 23 may have a width W of 20 to 80 mm. The waist band 23 is constructed of laminated sheets of nonwoven fabric 31 and plastic film 32 as basic material. These laminated sheets are partially welded together (as designated by reference numeral 33) so that these basic material may present a relatively low rigidity in the bridge-like area 28. It will be apparent to those skilled in the art that said laminated sheets may be entirely welded together without increasing the rigidity. In the adhesive sub-area 29 and the handling sub-area 30, on the other hand, these laminated sheets are not only welded together but also densely embossed (as designated by reference numeral 34) to impart the them a relatively high rigidity. Such thermal embossing causes the plastic film 32 to be at least partially melted and thereby to enter into spaces among fibres of the nonwoven fabric integrally with said nonwoven fabric 31. As a result, the adhesive sub-area 29 and the handling sub-area 30 obtain desired rigidities which will be described more in detail later and the interstices among fibres of the nonwoven fabric 31 are filled so as to facilitate application of adhesive which will be also described in detail later and to improve a strength of said nonwoven fabric 31. To obtain the basic material 35 of the waist band 23 including such adhesive sub-area 29 and handling sub-area 30, the nonwoven fabric 31 is that which has a METSUKE or weight per unit area of 20 to 40 g/m$^2$ and a density of 0.1 to 0.3 g/cm$^3$ and is composed of polyester, nylon, polypropylene, rayon fibres or like or a mixture thereof while the plastic film 32 is that which has a thickness of 20 to 60$\mu$ and a density of 0.91 to 0.97 g/cm$^3$ and is made of material having a melting point lower than that of said fibres, such as polyethylene, polypropylene or polyurethane (including a foamed type) in this preferred embodiment. These nonwoven fabric 31 and plastic film 32 may be superposed on one another and bonded together under a pressure by a pressure member carrying an embossing mold heated to a temperature close to the melting point of this film. However, such embossing is not critical for the present invention, so far as the plastic film 32 has been at least partially melted into the interstices among fibres of the nonwoven fabric 31 and thereby a desired high rigidity, as will be mentioned later again, has been imparted to the adhesive sub-area 29 and the handling sub-area 30. To obtain a desired integrated state without embossing the basic material 35, said sub-areas of the basic material 35 may be pressed by a hot flat roller.

The basic material 35 thus obtained is coated and immersed on the upper surface of the nonwoven fabric 31 in the bridge-like area 28 with a well known release agent such as silicone to form a release layer 36 and on the upper surface of the nonwoven fabric 31 in the adhesive sub-area 29 with pressure-sensitive adhesive to form an adhesive layer 37 of 30 to 160 g/m$^2$. An amount of release agent applied on the nonwoven fabric 31 to form said release layer 36 is so regulated that a desired release function may be obtained without increasing the rigidity of the nonwoven fabric 31. So far as such requirement is met, the bridge-like area 28 may be entirely coated with release agent and said requirement is met when the coating is formed with a thickness less than 20$\mu$. Furthermore, it is unnecessary to form the release layer 36 as a continuous layer so long as this layer 36 has a desired release ability. Instead, the nonwoven fabric 31 may have fibres here and there intermittently immersed with release agent or partially exposed. In the waist band 23 thus constructed, it is preferred that the bridge-like area 28 has a rigidity of 0.27 to 33.8, the adhesive sub-area 29 and the handling sub-area 30 have a rigidity of 2.16 to 15.6, and said bridge-like area 28 has a tensile strength of 4 kg/50 mm or higher. Said rigidities are given as measured by the method A according to the Japanese Industrial Standard (JIS) p 8143-1967 while said tensile strengths are given as measured by placing a sample piece of 50 mm in tension at a rate of 30 cm/min in the tension tester.

FIGS. 7A and 7B illustrate another manner in which the adhesive sub-area 29 and the handling sub-area 30 are constructed. In this manner, one end of the basic material 35 is folded back, as seen in FIG. 7A, so as to bring the plastic film 32 in contact with itself, then subjected to the previously described process of densely embossing and thereby said plastic film 32 is melted into the nonwoven fabric 31 on the upper and lower sides integrally therewith (see FIG. 7B). In this way, a desired rigidity can be imparted to the adhesive sub-area 29 and the handling sub-area 30 even when the nonwoven fabric 31 of a low METSUKE and a low density and the plastic film 32 of extremely small thickness and a low density are employed. Substantially same effect as obtained in this manner of construction can be obtained also when the plastic film 32 is sandwitched between two sheets of nonwoven fabric 31 not shown. In such a case also, the components may be merely welded together without said embossing.

Figure 5:
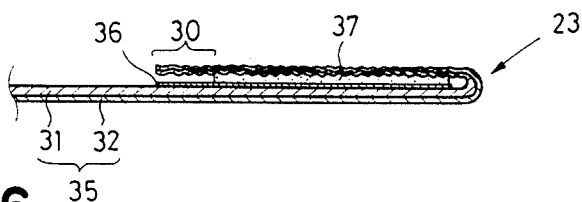
FIG. 5 is a schematic section in an enlarged scale taken along a line 5—5 in FIG. 4.
Figure 6:
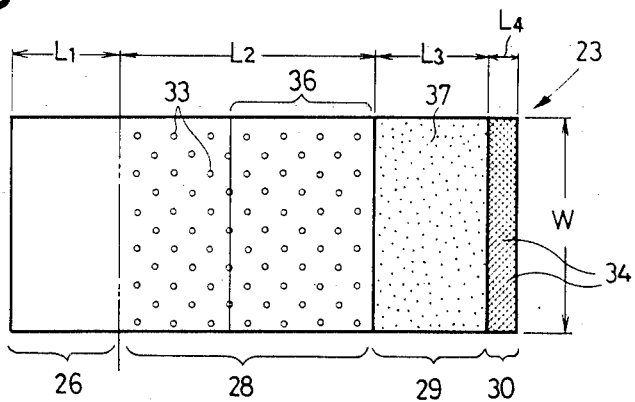
FIG. 6 is a developed plan view illustrating an embodiment of the waist band constructed according to the present invention.

In the waist band 23 thus constructed, the outer end is folded back when not used so that the adhesive layer 37 is provisionarily attached to the release layer 36, as seen in FIG. 5, and the handling sub-area 30 may be held between fingers and peeled off from the release layer 36 (see FIG. 6), when used.

Figure 4:
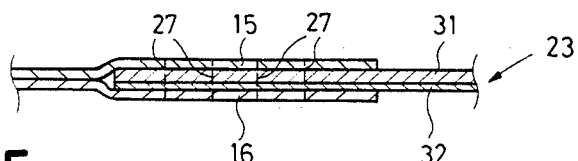
FIG. 4 is a schematic section in an enlarged scale taken along a line 4—4 in FIG. 3.

The waist band 23 of the invention constructed as has been described hereinabove is advantageous in that, when the diaper 11 is put on the user with the adhesive sub-area 29 of the waist band 23 being adhesively fastened to the backsheet 16, the bridge-like area 28 extending between the attachment area 26 fixed to the diaper and the adhesive sub-area 29 is easily deformable in every direction and maintained in soft contact with the user's body, since said bridge-like area 28 has not only a low rigidity (or high flexibility) but also more or less elasticity and the nonwoven fabric 31 is positioned to confront the user's body (see FIGS. 4 and 5). The waist band 23 is convenient also in that the waist size can be adjusted to the individual users, since the bridge-like area 28 has an adequate length for such adjustment. The fact that the adhesive sub-area 29 and the handling sub-area 30 of the waist band 23 have an adequately high rigidity not only facilitates fastening and peeling operation with respect to the backsheet 16 but also assures a fastening effect of said adhesive sub-area 29 with respect to said backsheet 16. Such reliable fastening effect is further assured by the fact that the bridge-like area 28 has a rigidity lower than that of the adhesive sub-area 29 and a force possibly exerted on the bridge-like area 28 due to a movement of the user is thereby reduced or absorbed. Furthermore, the handling area 30, if embossed, has a rough surface serving to prevent the fingers from a slippage during said operation of fastening and peeling. Said operation is thus further facilitated.

FIGS. 8A, 8B and 8C respectively illustrate manners in which a plurality of slits 38 are formed transversely of the waist band 23 in the adhesive sub-area 29, the bridge-like area 28, and in both said bridge-like area and said adhesive sub-area, respectively, wherein these slits 38 extend through the respective areas or sub-area from the upper surface to the lower surface. These slits 38 may be replaced by a central single slit and may be intermittent or continuous.

When the diaper is put on the user, it can be considered that the waist band 23 is exposed to various forces occrring due to a movement of the user such as shearing force, peeling force and deforming force, so it is feared that the adhesive sub-area 29 might be peeled off from the backsheet, when said various forces excess certain critical levels. However, provision of said slits 38 in the bridge-like area 28 and/or the adhesive sub-area 29 permits respective portions of these area and/or sub-area isolated by said slits 38 to function independently of others and, in consequence, said forces exerted on the bridge-like area 28 and sid adhesive sub-area 29 can be effectively dispersed or absorbed.

Figure 9A:
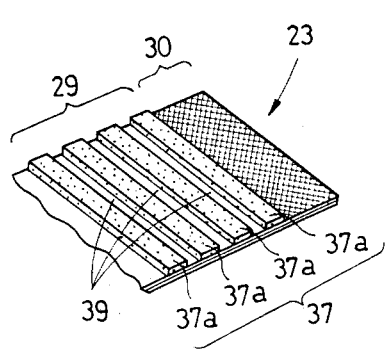
FIG. 9A is a fragmentary perspective view illustrating a manner in which said adhesive sub-area is realized as a plurality of intermittently arranged adhesive stripes.
Figure 9B:
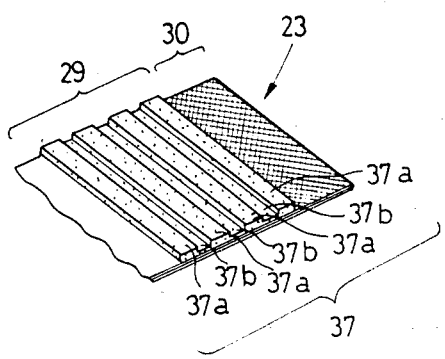
FIG. 9B is a view similar to FIG. 9A but illustrating another embodiment of said adhesive sub-area.

FIGS. 9A and 9B illustrate a variation of the adhesive sub-area 29. In this variation, the adhesive sub-area 29 is so formed that the adhesive layer 37 may be intermittently present longitudinally of the waist band 23, i.e., ridges 37 of said adhesive layer and grooves 39 in which no adhesive layer is present may be alternately arranged. These ridges and grooves thus alternately arranged are individually designated by 37a and 37b in FIG. 9. Depending on the dimensional condition of the adhesive sub-area 29, each ridge 37a is 3 to 10 mm wide and each groove 37b or 39 is 1 to 5 mm wide. Total area occupied by the grooves 37a or 39 is less than 50%, preferably from 10 to 30% of the adhesive sub-area 29 as a whole.

Conventionally, flexible plastic film of polyethylene or like has been employed as the backsheet 16 of the diaper and the backsheet 16 has often been stretched or even damaged when the adhesive sub-area 29 of the waist band 23 is peeled off from the backsheet 16 to check presence or absence of excrement or to readjust a waist line fitness. According to the present invention, however, this inconvenience is avoided, since the surface of the adhesive layer 37 to be adhered to the backsheet 16 is intermittently formed longitudinally of the waist band 23 as previously described.

What is claimed is:

1. A disposable diaper comprising a facing sheet defining a diaper inside surface for direction towards an infant, a moisture-impervious backing sheet substantially coextensive with said facing sheet and defining a diaper outside surface, an absorbent layer positioned between said facing sheet and said backing sheet, said facing sheet and backing sheet being configured so as to form a front panel and a back panel, and fastening means connected together said front and back panels at the waist portion of said diaper, the improvement comprising (a) that said fastening means is in the form of an elongated strip and is composed of coextensive laminated layers of (1) plastic film and (2) non-woven fabric, said non-woven fabric being positioned so that it will be facing the body of the diaper wearer,
    (b) that said fastening means holds said front and back panels together in a non-overlapping spaced-apart relationship and the space that is left between said front and back panels is spanned by an intermediate bridge-like portion of said fastener means, said bridge-like portion having a length of 40–80 mm and being laminated together only at spaced apart points so as to give it greater flexibility than the fully laminated portions extending outwardly from both ends of said bridge-like portion,
    (c) that one end of said fastening means is joined to said back panel by permanent bonding,
    (d) that the other end of said fastening means is adhesively secured to said front panel by an adhesive section located on said fastening means, and
    (e) that said fastening means has a handling portion of 5–15 mm length extending outwardly from said adhesive section which permits easy and quick disengagement of the fastening means from the rest of the diaper, said handling section being free from adhesive on either side thereof.

2. A disposable diaper according to claim 1 wherein said bridge-like portion contains a plurality of slits that extend to opposite ends of said fastening means.

3. A diaper according to claim 1 wherein the width of said fastener means is 20–80 mm.

4. A diaper according to claim 3 wherein the length of said adhesive section is 20–40 mm.

5. A diaper according to claim 1 wherein said adhesive section consists of a plurality of parallel spaced apart narrow strips of adhesive.

6. A diaper according to claim 1 wherein the permanent bonding of (c) consists of one end of said fastening means being sandwiched between a facing sheet portion and a backing sheet portion of said back panel.

* * * * *